(12) United States Patent
Won et al.

(10) Patent No.: US 11,489,130 B2
(45) Date of Patent: Nov. 1, 2022

(54) QUANTUM-DOT LIGHT EMITTING DIODE AND QUANTUM-DOT LIGHT EMITTING DISPLAY DEVICE INCLUDING THE SAME

(71) Applicant: LG DISPLAY CO., LTD., Seoul (KR)

(72) Inventors: Jeong-Eun Won, Paju-si (KR); Seul-Gi Choi, Paju-si (KR)

(73) Assignee: LG Display Co., Ltd., Seoul (KR)

( * ) Notice: Subject to any disclaimer, the term of this patent is extended or adjusted under 35 U.S.C. 154(b) by 115 days.

(21) Appl. No.: 17/023,809

(22) Filed: Sep. 17, 2020

(65) Prior Publication Data
US 2021/0098727 A1  Apr. 1, 2021

(30) Foreign Application Priority Data
Oct. 1, 2019  (KR) .................. 10-2019-0121690

(51) Int. Cl.
*H01L 51/50* (2006.01)
*H01L 27/32* (2006.01)
*H01L 51/00* (2006.01)

(52) U.S. Cl.
CPC ........ *H01L 51/502* (2013.01); *H01L 27/3211* (2013.01); *H01L 51/0059* (2013.01); *H01L 51/0061* (2013.01); *H01L 27/3244* (2013.01); *H01L 51/0072* (2013.01); *H01L 2251/303* (2013.01); *H01L 2251/552* (2013.01)

(58) Field of Classification Search
CPC ............... H01L 51/502; H01L 27/3211; H01L 51/0059; H01L 51/0061; H01L 51/0072
See application file for complete search history.

(56) References Cited

U.S. PATENT DOCUMENTS

2018/0138434 A1* 5/2018 Yoon ................... H01L 29/6609

* cited by examiner

*Primary Examiner* — Anthony Ho
(74) *Attorney, Agent, or Firm* — Morgan, Lewis & Bockius LLP

(57) ABSTRACT

The present disclosure provides a quantum dot (QD) light emitting diode including: a first electrode and a second electrode facing each other; a QD emitting material layer positioned between the first electrode and the second electrode and including a QD; a hole auxiliary layer positioned between the first electrode and the QD emitting material layer; and an electron transporting layer positioned between the QD emitting material layer and the second electrode and including an electron-property material and a hole-property material.

20 Claims, 16 Drawing Sheets

100

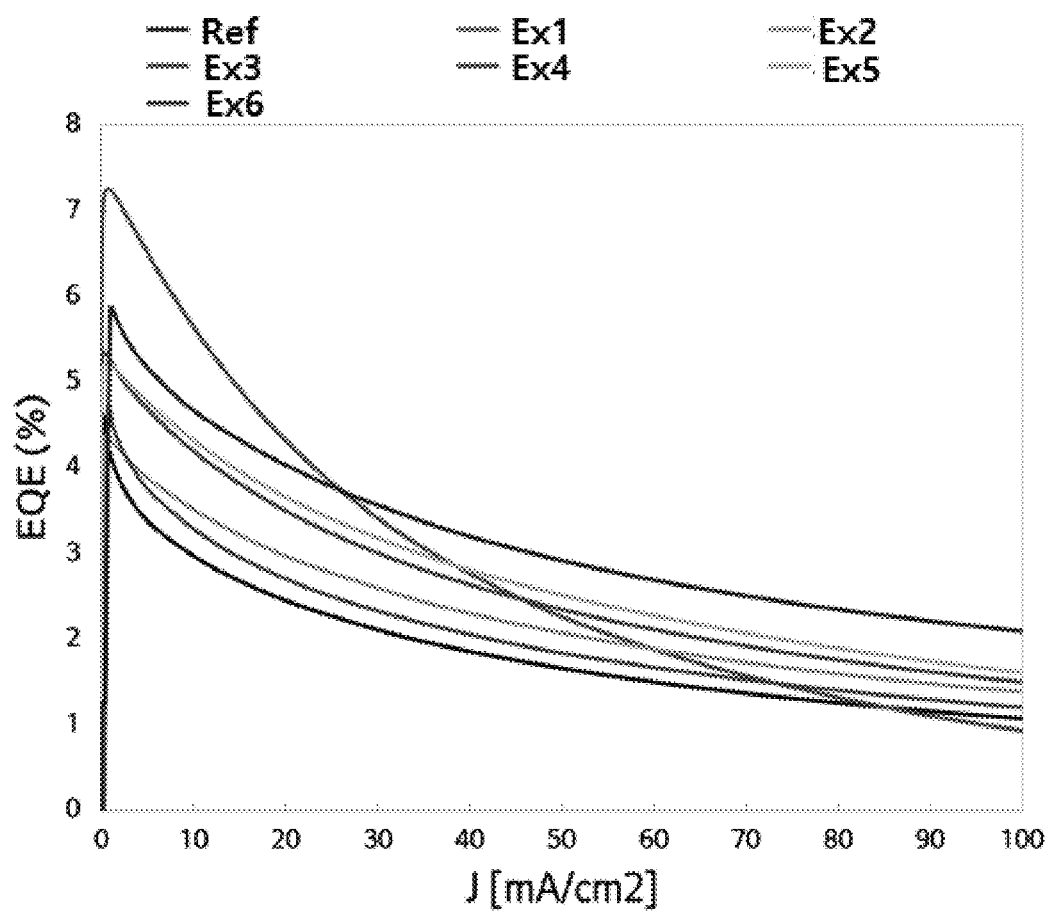

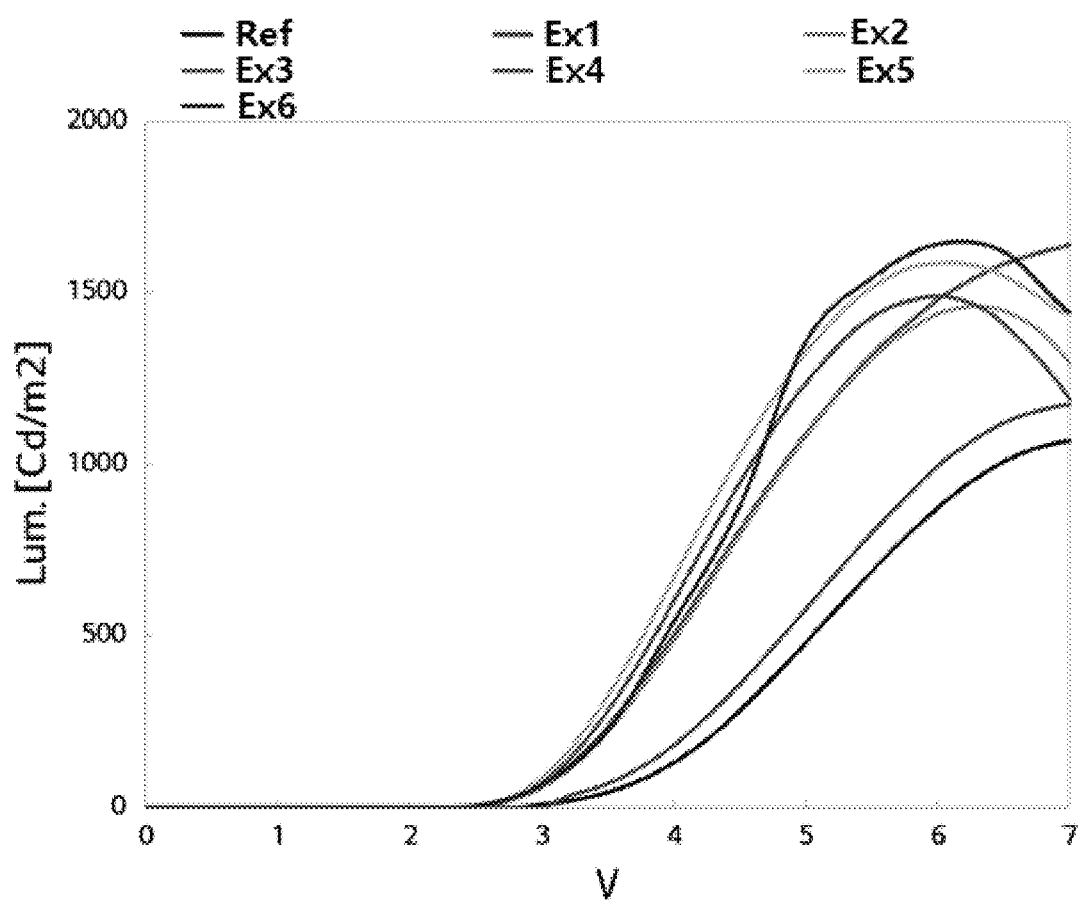

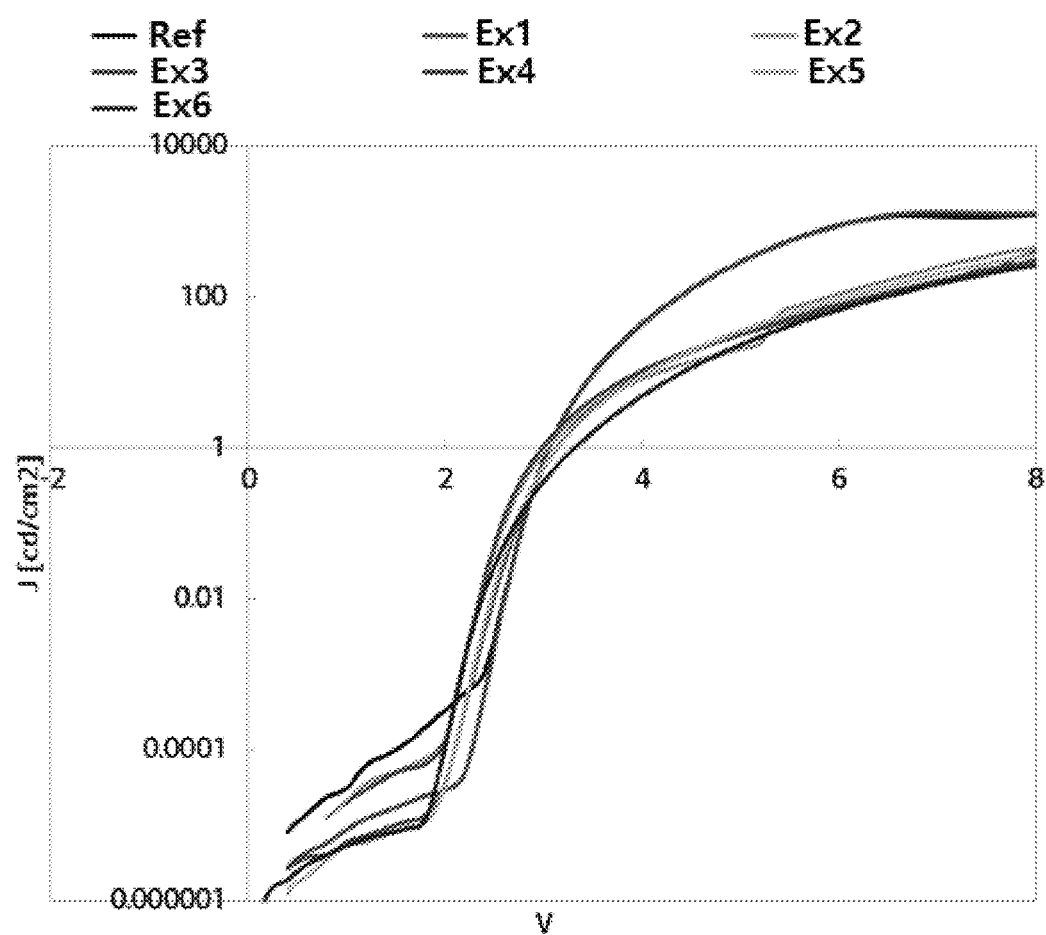

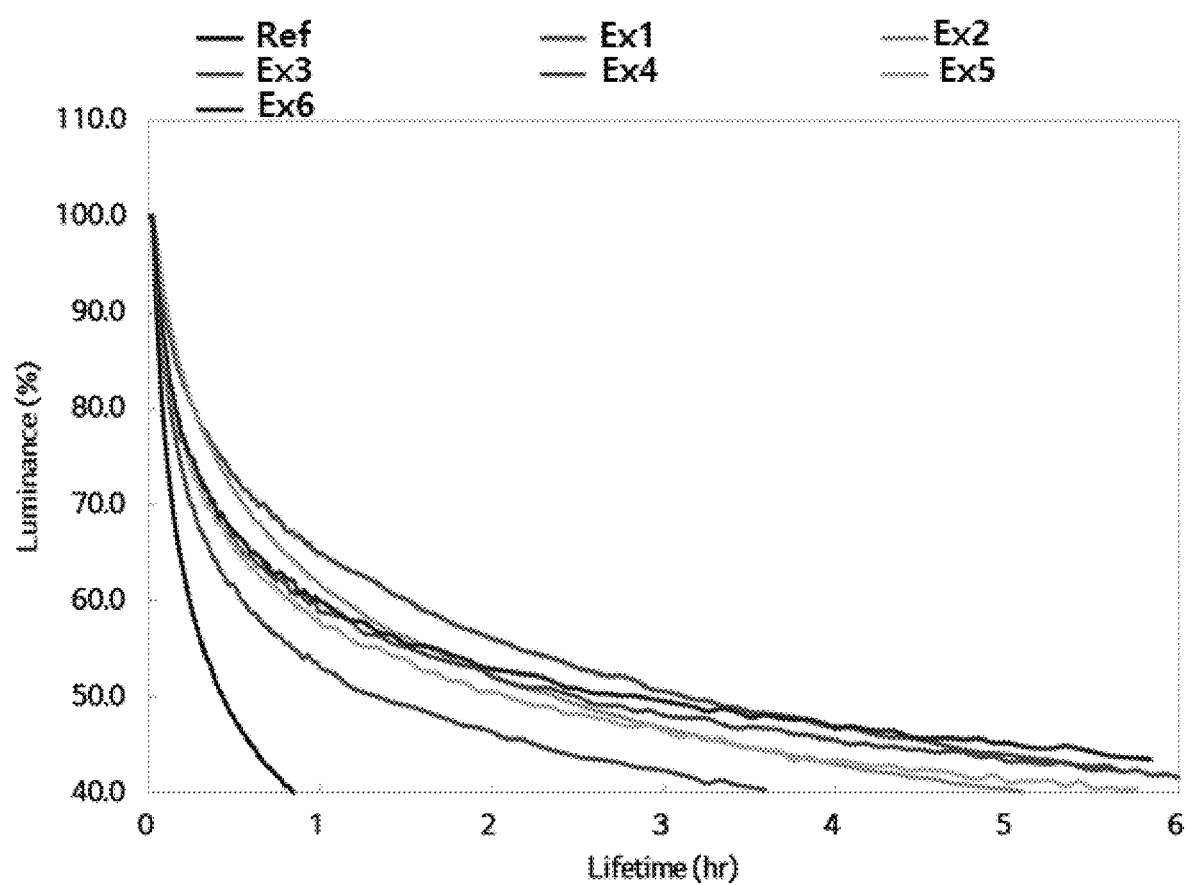

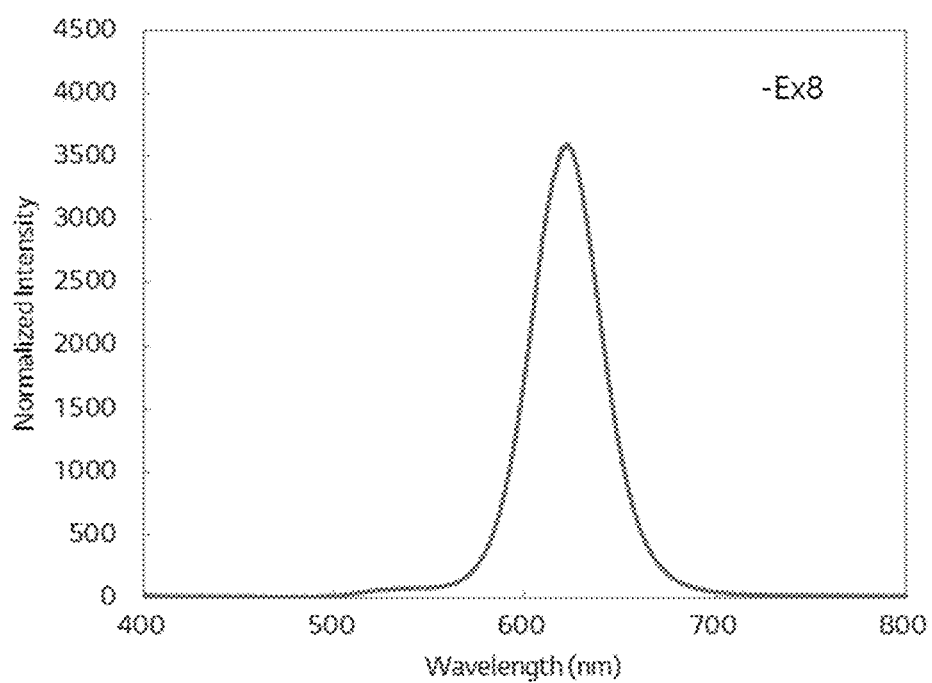

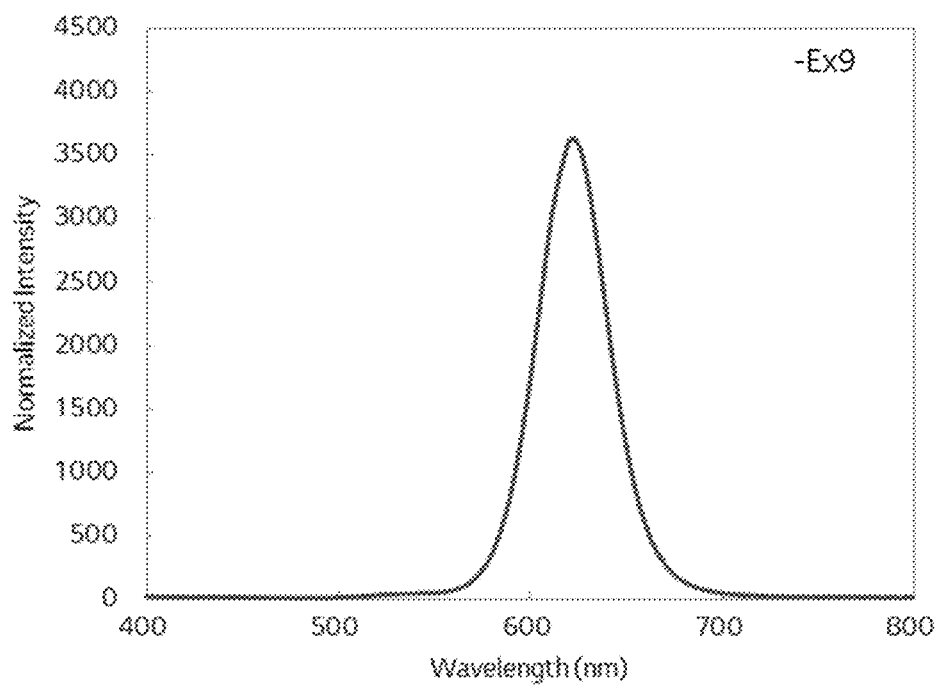

QUANTUM-DOT LIGHT EMITTING DIODE AND QUANTUM-DOT LIGHT EMITTING DISPLAY DEVICE INCLUDING THE SAME

CROSS-REFERENCE TO RELATED APPLICATIONS

This application claims priority to and the benefit of Republic of Korea Patent Application No. 10-2019-0121690 filed in the Republic of Korea on Oct. 1, 2019, which is hereby incorporated by reference.

BACKGROUND

Technical Field

The present disclosure relates to a quantum-dot (QD) light emitting diode, and more particularly, to a QD light emitting diode and a QD light emitting display device having improved charge balance and high emitting efficiency.

Discussion of the Related Art

Recently, as society has entered in earnest upon an information age, a field of display devices that represent all sorts of electrical signals as visual images has been developed rapidly. For example, a flat panel display device, such as a liquid crystal display (LCD) device, a plasma display panel (PDP) device, a field emission display (FED) device, and an organic light emitting diode (OLED) device, has been introduced.

On the other hand, use of quantum dots (QD) to display devices has been researched or studied.

In the QD, an electron in unstable state transitions from a conduction band to a valence band such that light is emitted. Since the QD has a high extinction coefficient and excellent quantum yield, strong fluorescent light is emitted from the QD. In addition, since the wavelength of the light from the QD is controlled by a size of the QD, entire visible light can be emitted by controlling the size of the QD.

The QD light emitting diode using the QD includes an anode, a cathode facing the anode and a QD emitting layer. The QD emitting layer is disposed between the anode and the cathode and includes the QD. When the hole and the electron are respectively injected from the anode and the cathode into the QD emitting layer, the light is emitted from the QD emitting layer.

However, in the related art QD light emitting diode, the QD has a deep highest occupied molecular orbital (HOMO) level such that the charge balance in the QD emitting layer and the emitting efficiency of the QD light emitting diode are decreased.

SUMMARY

Accordingly, embodiments of the present disclosure are directed to a QD light emitting diode, a QD light emitting display device and a method of fabricating the QD light emitting diode that substantially obviate one or more of the problems due to limitations and disadvantages of the related art, and have other advantages.

Additional features and aspects will be set forth in the description that follows, and in part will be apparent from the description, or may be learned by practice of the inventive concepts provided herein. Other features and aspects of the inventive concepts may be realized and attained by the structure particularly pointed out in the written description, or derivable therefrom, and the claims hereof as well as the appended drawings.

To achieve these and other aspects of the inventive concepts, as embodied and broadly described, a quantum dot (QD) light emitting diode comprises: a first electrode and a second electrode facing each other; a QD emitting material layer positioned between the first electrode and the second electrode and including a QD; a hole auxiliary layer positioned between the first electrode and the QD emitting material layer; and an electron transporting layer positioned between the QD emitting material layer and the second electrode and including an electron-property material and a hole-property material.

In another aspect, a QD light emitting display device comprises: a substrate including a red pixel region, a green pixel region and a blue pixel region; a QD light emitting diode positioned on or over the substrate, the QD light emitting diode including: a first electrode and a second electrode facing each other; a QD emitting material layer positioned between the first electrode and the second electrode and including a QD; a hole auxiliary layer positioned between the first electrode and the QD emitting material layer; and an electron transporting layer positioned between the QD emitting material layer and the second electrode; and a thin film transistor positioned between the substrate and the QD light emitting diode and connected to the QD light emitting diode, wherein the electron transporting layer in the red pixel region includes an electron-property material and a hole-property material.

It is to be understood that both the foregoing general description and the following detailed description are examples and are explanatory and are intended to provide further explanation of the invention as claimed.

BRIEF DESCRIPTION OF THE DRAWINGS

The accompanying drawings, which are included to provide a further understanding of the disclosure and are incorporated in and constitute a part of this application, illustrate aspect of the disclosure and together with the description serve to explain principles of the disclosure.

FIGS. 7A to 7D are graphs showing an emission property of a QD light emitting diode of the present disclosure.

FIGS. 8A to 8G are graphs showing an emission property of a QD light emitting diode of the present disclosure.

DETAILED DESCRIPTION

Reference will now be made in detail to aspect of the disclosure, examples of which are illustrated in the accompanying drawings.

Figure 1:
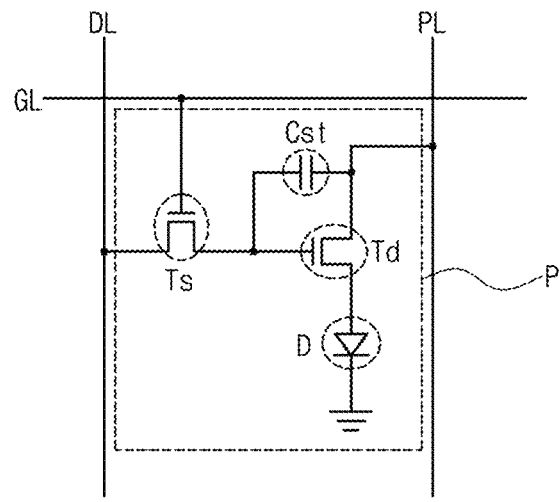
FIG. 1 is a schematic circuit diagram of a QD light emitting display device according to the present disclosure.

FIG. 1 is a schematic circuit diagram of a QD light emitting display device according to the present disclosure.

As shown in FIG. 1, in a QD light emitting display device, a gate line GL, a data line DL and a power line PL are formed, and a pixel region P is defined by the gate and data lines GL and DL. In the pixel region P, a switching thin film transistor (TFT) Ts, a driving TFT Td, a storage capacitor Cst and a QD light emitting diode D are formed.

The switching TFT Ts is connected to the gate line GL and the data line DL, and the driving TFT Td and the storage capacitor Cst are connected to the switching TFT Ts and the power line PL. The QD light emitting diode D is connected to the driving TFT Td.

In the QD display device, when the switching TFT Ts is turned on by a gate signal applied through the gate line GL, a data signal from the data line DL is applied to a gate electrode of the driving TFT Td and an electrode of the storage capacitor Cst through the switching TFT Ts.

When the driving TFT Td is turned on by the data signal, an electric current is supplied to the QD light emitting diode D from the power line PL through the driving TFT Td. As a result, the QD light emitting diode D emits light. The storage capacitor Cst serves to maintain the voltage of the gate electrode of the driving TFT Td for one frame.

Accordingly, the QD light emitting display device displays images.

Figure 2:
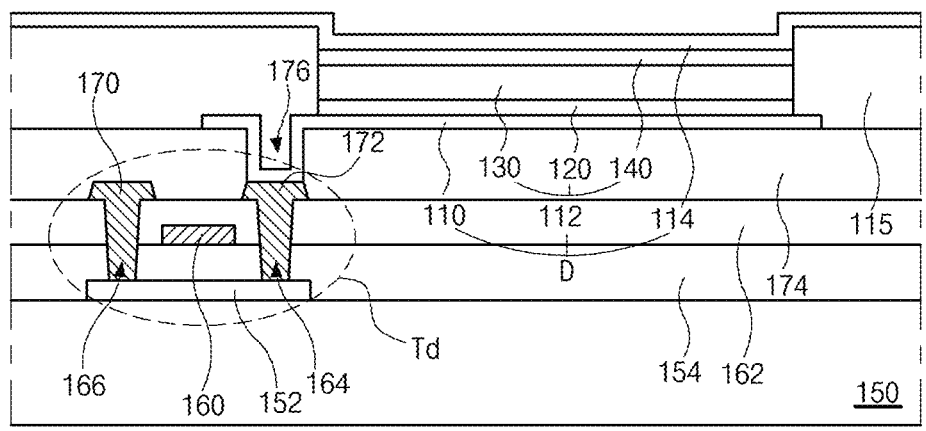
FIG. 2 is a schematic cross-sectional view of a QD light emitting display device of the present disclosure.

FIG. 2 is a schematic cross-sectional view of a QD light emitting display device of the present disclosure.

As shown in FIG. 2, the QD light emitting display device 100 includes a substrate 150, the TFT Td on the substrate 150 and the QD light emitting diode D over the substrate 150 and connected to the TFT Td.

In FIG. 2, a single pixel region is shown. Alternatively, the QD light emitting display device may include a red pixel region, a green pixel region and a blue pixel region, and each of the TFT Td and the QD light emitting diode D may be disposed in each of the red, green and blue pixel regions.

The substrate 150 may be a glass substrate or a flexible substrate of polyimide. The substrate 150 may have a flexible property.

Although not shown, a buffer layer of an inorganic material, e.g., silicon oxide or silicon nitride, may be formed on the substrate 150.

The TFT Td is connected to the switching TFT Ts (of FIG. 1) and includes a semiconductor layer 152, a gate electrode 160, a source electrode 170 and a drain electrode 172.

The semiconductor layer 152 is formed on the substrate 150. The semiconductor layer 152 may be formed of an oxide semiconductor material or a poly-silicon.

When the semiconductor layer 152 includes the oxide semiconductor material, a light-shielding pattern (not shown) may be formed under the semiconductor layer 152. The light to the semiconductor layer 152 is shielded or blocked by the light-shielding pattern such that thermal degradation of the semiconductor layer 152 can be prevented. On the other hand, when the semiconductor layer 152 includes polycrystalline silicon, impurities may be doped into both sides of the semiconductor layer 152.

A gate insulating layer 154 is formed on the semiconductor layer 152. The gate insulating layer 154 may be formed of an inorganic insulating material such as silicon oxide or silicon nitride.

A gate electrode 160, which is formed of a conductive material, e.g., metal, is formed on the gate insulating layer 154 to correspond to a center of the semiconductor layer 152. The gate electrode 160 is connected to the switching TFT.

The gate insulating layer 154 is formed on the entire surface of the substrate 150. Alternatively, the gate insulating layer 154 may be patterned to have the same shape as the gate electrode 160.

An interlayer insulating layer 162, which is formed of an insulating material, is formed on an entire surface of the substrate 150 including the gate electrode 160. The interlayer insulating layer 162 may be formed of an inorganic insulating material, e.g., silicon oxide or silicon nitride, or an organic insulating material, e.g., benzocyclobutene or photo-acryl.

The interlayer insulating layer 162 includes first and second contact holes 166 and 164 exposing both sides of the semiconductor layer 152. The first and second contact holes 166 and 164 are positioned at both sides of the gate electrode 160 to be spaced apart from the gate electrode 160.

The first and second contact holes 166 and 164 extend into the gate insulating layer 154. Alternatively, when the gate insulating layer 154 is patterned to have the same shape as the gate electrode 160, there may be no first and second contact holes 166 and 164 in the gate insulating layer 154.

A source electrode 170 and a drain electrode 172, which are formed of a conductive material, e.g., metal, are formed on the interlayer insulating layer 162. The source electrode 170 and the drain electrode 172 are spaced apart from each other with respect to the gate electrode 160 and respectively contact both sides of the semiconductor layer 152 through the first and second contact holes 166 and 164. The source electrode 170 is connected to the power line PL (of FIG. 1).

The TFT Td including the semiconductor layer 152, the gate electrode 160, the source electrode 170 and the drain electrode 172 serves as a driving element.

The gate electrode 160, the source electrode 170 and the drain electrode 172 are positioned over the semiconductor layer 152. Namely, the TFT Td has a coplanar structure.

Alternatively, in the TFT Td, the gate electrode may be positioned under the semiconductor layer, and the source and drain electrodes may be positioned over the semiconductor layer such that the TFT Td may have an inverted staggered structure. In this instance, the semiconductor layer may include amorphous silicon.

On the other hand, the switching TFT Ts (of FIG. 1) may have substantially same structure as the TFT Td.

A passivation layer 174, which includes a drain contact hole 176 exposing the drain electrode 172 of the TFT Td, is formed to cover the TFT Td.

A first electrode 110, which is connected to the drain electrode 172 of the TFT Td through the drain contact hole 176, is separately formed on the passivation layer 174 in each pixel region. The first electrode 110 may be an anode and may be formed of a conductive material having a relatively high work function. For example, the first electrode 110 may be formed of a transparent conductive material such as indium-tin-oxide (ITO) or indium-zinc-oxide (IZO).

When the QD display device 100 of the present disclosure is a top-emission type, a reflection electrode or a reflection layer may be formed under the first electrode 110. For example, the reflection electrode or the reflection layer may be formed of aluminum-palladium-copper (APC) alloy.

A bank layer 115, which covers edges of the first electrode 110, is formed on the passivation layer 174. The bank 115 exposes a center of the first electrode 110 in the pixel region.

An emitting layer 112 is formed on the first electrode 110. The emitting layer 112 includes a QD emitting material layer (QD EML) 130, a hole auxiliary layer 120 under the QD EML 130 and an electron auxiliary layer 140 over the QD EML 130.

A second electrode 114 is formed over the substrate 150 including the emitting layer 112. The second electrode 114 is positioned at an entire surface of the display area. The second electrode 114 may be a cathode and may be formed of a conductive material having a relatively low work function. For example, the second electrode 114 may be formed of aluminum (Al), silver (Ag), gold (Au), magnesium (Mg) or Al—Mg alloy.

The hole auxiliary layer 120 is positioned between the first electrode 110 and the QD EML 130, and the electron auxiliary layer 140 is positioned between the QD EML 130 and the second electrode 114.

The first electrode 110, the emitting layer 112 and the second electrode 114 constitute the QD light emitting diode D.

Although not shown, an encapsulation film for preventing moisture and/or oxygen penetration may be formed on or over the second electrode (114). For example, the encapsulation film may have a stack structure of a first inorganic layer, an organic layer and a second inorganic layer, but it is not limited thereto.

In addition, a polarizing plate for reducing an ambient light reflection may be attached to a display surface of the QD light emitting display device. For example, the polarizing plate may be a circular polarizing plate.

Figure 3:
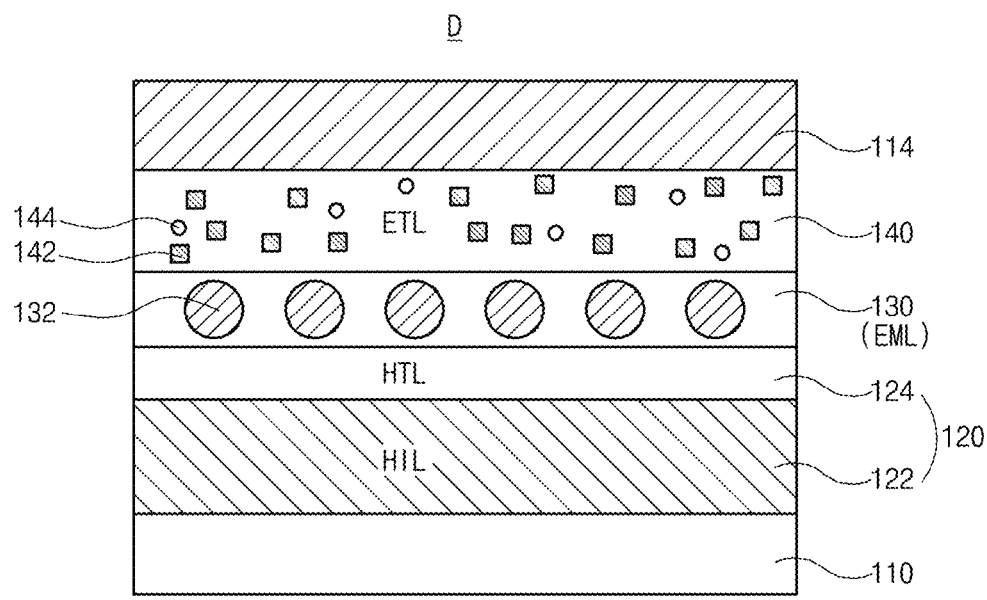
FIG. 3 is a schematic cross-sectional view of a QD light emitting diode according to a first embodiment of the present disclosure.

FIG. 3 is a schematic cross-sectional view of a QD light emitting diode according to a first embodiment of the present disclosure.

As shown in FIG. 3, the QD light emitting diode D of the present disclosure includes a first electrode 110, a second electrode 114 facing the first electrode 110 and an emitting layer 112 between the first and second electrodes 110 and 114. The emitting layer 112 includes a QD EML 130, a hole auxiliary layer 120 between the first electrode 110 and the QD EML 130 and an electron auxiliary layer 140 as an electron transporting layer between the QD EML 130 and the second electrode 114.

The first electrode 110 may be an anode, and the second electrode 114 may be a cathode.

The QD EML 130 includes a plurality of QDs 132. Each QD 132 is formed of a semiconductor material. The QD 132 includes a core, which is positioned in a center of the QD 180 and emits light, and a shell surrounding (or enclosing) the core. The QD 180 may further include a ligand connected to (or combined with) a surface of the shell.

The core and the shell have a difference in an energy bandgap. Each of the core and the shell may include a nano-size semiconductor material of II-VI group element or III-V group element. For example, the nano-size semiconductor material may be one of CdSe, CdS, CdTe, ZnSe, ZnTe, ZnS, HgTe, InAs, InP, GaAs and GaP.

For example, the QD 132 may have a structure of ZnSe/ZnS, CdSe/CdS, CdSe/ZnS, CdSe/ZnSe, CdTe/CdS, CdTe/ZnS, CdTe/ZnSe, CdS/ZnS, CdS, ZnSe, InP/CdS, InP/ZnS or InP/ZnSe.

The ligand may be C1 to C30 alkyl group, and the QD 180 may be dispersed in a solvent due to the ligand. Accordingly, the QD EML 130 may be formed by a solution process.

The hole auxiliary layer 120 may include a hole transporting layer (HTL) 124 between the first electrode 110 and the QD EML 130 and a hole injection layer (HIL) 122 between the first electrode 110 and the HTL 124. One of the HIL 122 and the HTL 124 may be omitted.

The electron auxiliary layer 140 may include an electron transporting layer (ETL) 142 between the QD EML 130 and the second electrode 114 and an electron injection layer (EIL) 144 between the ETL 142 and the second electrode 114.

For example, the HIL 122 may be formed of an organic hole injection material, e.g., PEDOT:PSS, and the HTL 124 may be formed of an organic hole transporting material, e.g., poly[(9,9-dioctylfluorenyl-2,7-diyl)-co-(4,4'-(N-(4-sec-butylphenyl)diphenylamine)] (TFB), poly(9-vinylcarbazole) (PVK), poly[9-sec-butyl-2,7-difluoro-9H-Carbazole] (2,7-F-PVF), poly[3-(carbazol-9-yl)-9-(3-methyloxetan-3-ylmethyl)carbazole] (PCOC), 9,9-bis[4-[(4-ethenylphenyl)methoxy]phenyl]-N2,N7-di-1-naphthalenyl-N2,N7-diphenyl-9H-Fluorene-2,7-diamine (VB-FNPD), 4,4'-bis(3-((4-vinylphenoxy)methyl)-9H-carbazol-9-yl)biphenyl (DV-CBP), N4,N4'-bis(4-(6-((3-ethyloxetan-3-yl)methoxy)hexyloxy)phenyl)-N4,N4'-bis(4-methoxyphenyl)biphenyl-4,4'-diamine (QUPD), poly[N,N-bis(4-butylphenyl)-N,N-bisphenylbenzidine] (p-TPD), N4,N4'-di(naphthalen-1-yl)-N4,N4'-bis(4-vinylphenyl)biphenyl-4,4'-diamine (VNPB), or tris(4-carbazoyl-9-ylphenyl)amine (TCTA). However, the materials of the HIL 122 and the HTL 124 are not limited thereto.

The ETL 140 is positioned between the QD EML 130 and the second electrode 114. For injecting an electron from the second electrode 114 into the QD EML 130, the ETL 140 includes an electron-property material (electron characteristic material) 142 of an inorganic material. For example, the electron-property material 142 may be a zinc-oxide material, e.g., ZnO or ZnMgO.

However, since the QD 132 of the QD EML 130 has a deep HOMO level, a hole injection rate from the first electrode 110 into the QD EML 130 is slower than an electron injection rate from the second electrode 114 into the QD EML 130. Accordingly, the charge balance in the QD light emitting diode D is destroyed, and the emitting efficiency and the lifespan of the QD light emitting diode D are decreased.

To prevent the above problems, the ETL 140 in the QD light emitting diode D of the present disclosure further includes a hole-property material (hole characteristic material) 144. Namely, the ETL 140 includes the electron-property material 142 having an electron mobility greater than a hole mobility and the hole-property material 144 having a hole mobility greater than an electron mobility. As a result, the electron injection rate from the second electrode 114 into the QD EML 130 is decreased such that the charge balance in the QD light emitting diode D is improved.

In the ETL 140, the electron-property material 142 has a weight ratio (weight %) greater than the hole-property material 144. For example, the weight ratio of the electron-property material 142 to the hole-property material 144 may be about 240:1 to about 6:1.

Figure 4:
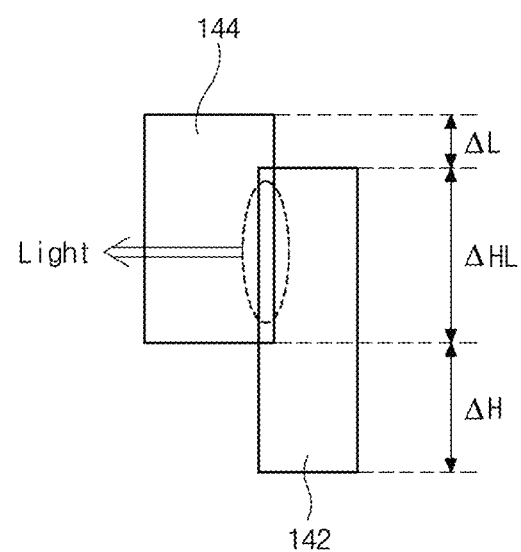
FIG. 4 is a schematic view for explaining a relation of an energy level of an electron-property material and a hole-property material in an electron transporting layer of a QD light emitting diode.

Referring to FIG. 4, which is a schematic view for explaining a relation of an energy level of an electron-property material and a hole-property material in an electron transporting layer of a QD light emitting diode, the HOMO level of the electron-property material 142 is lower than that of the hole-property material 144, and a lowest unoccupied molecular orbital (LUMO) level of the electron-property material 142 is lower than that of the hole-property material 144.

For example, a HOMO level difference ($\Delta H$) between the electron-property material 142 and the hole-property material 144 may be about 0.9 to 1.6 eV, a LUMO level difference (ΔL) between the electron-property material 142 and the hole-property material 144 may be about 1.3 to 2 eV.

The hole-property material 144 may be at least one of TCTA, p-TPD, m-MTDATA, TFB, PVK and VNPB of Formulas 1 to 6. In Formulas 2, 4 and 5, "n" is an integer of 1 to 10000.

[Formula 1]

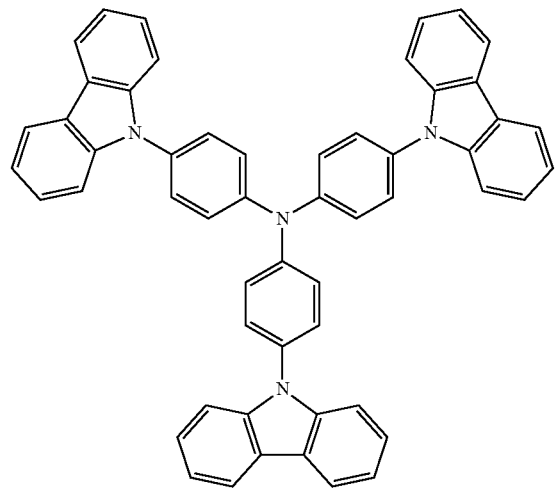

[Formula 2]

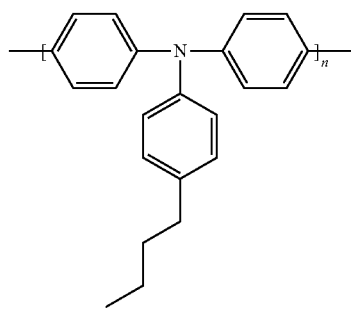

[Formula 3]

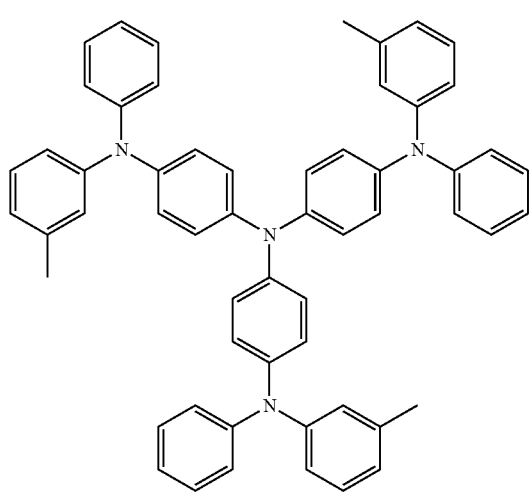

[Formula 4]

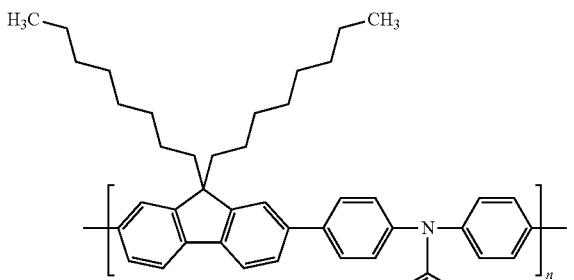

[Formula 5]

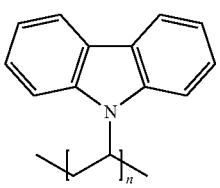

[Formula 6]

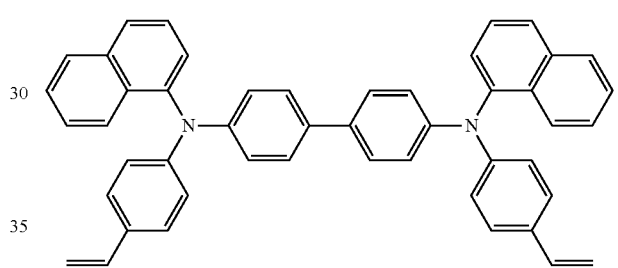

The energy levels of ZnMgO (as the electron-property material 142), TCTA, p-TPD, m-MTDATA, TFB, PVK and VNPB (as the hole-property material 144) are measured and listed in Table1.

TABLE 1

|  | LUMO (eV) | HOMO (eV) |
|---|---|---|
| ZnMgO | −3.6 | −7.1 |
| TCTA | −2.7 | −5.8 |
| p-TPD | −2.4 | −5.3 |
| m-MTDATA | −2.0 | −5.1 |
| TFB | −2.3 | −5.3 |
| PVK | −2.4 | −5.6 |
| VNPB | −2.4 | −5.3 |

A difference (ΔHL) between the HOMO level of the hole-property material 144 and the LUMO level of the electron-property material 142 may be about 1.5 to 2.5 eV, and preferably, about 1.5 to 2.2 eV. In this case, the electron-property material 142 and the hole-property material 144 form an exciplex such that the light having a peak wavelength of about 500 to 850 nm is emitted from the ETL 140.

Figure 5A:
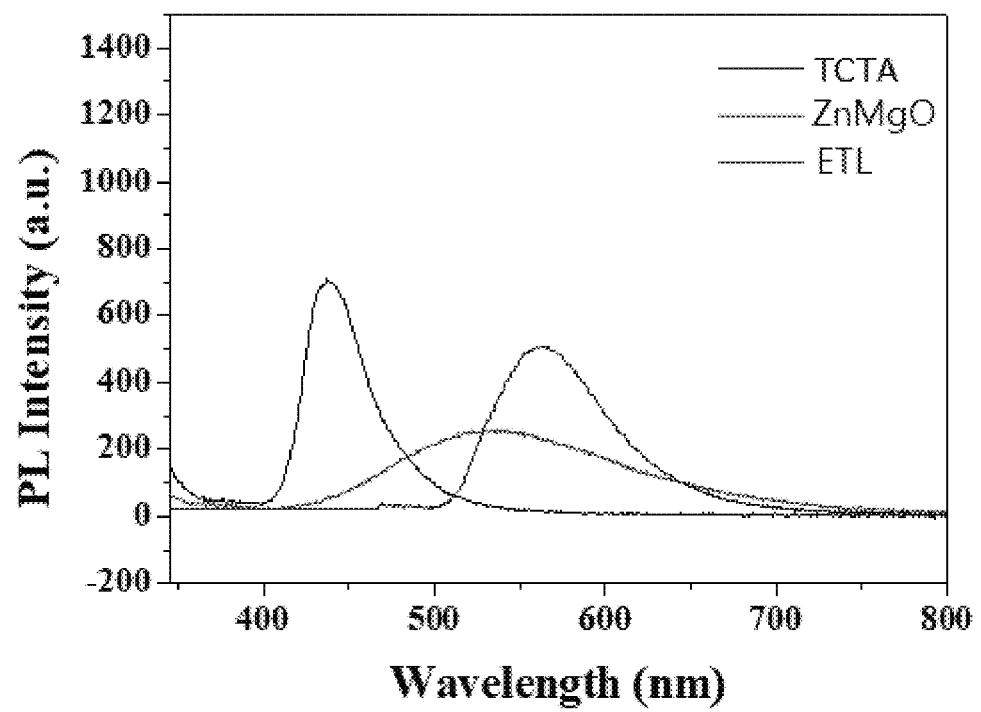
FIGS. 5A to 5C are graphs showing an exciplex emission property in an electron transporting layer of a QD light emitting diode.
Figure 5B:
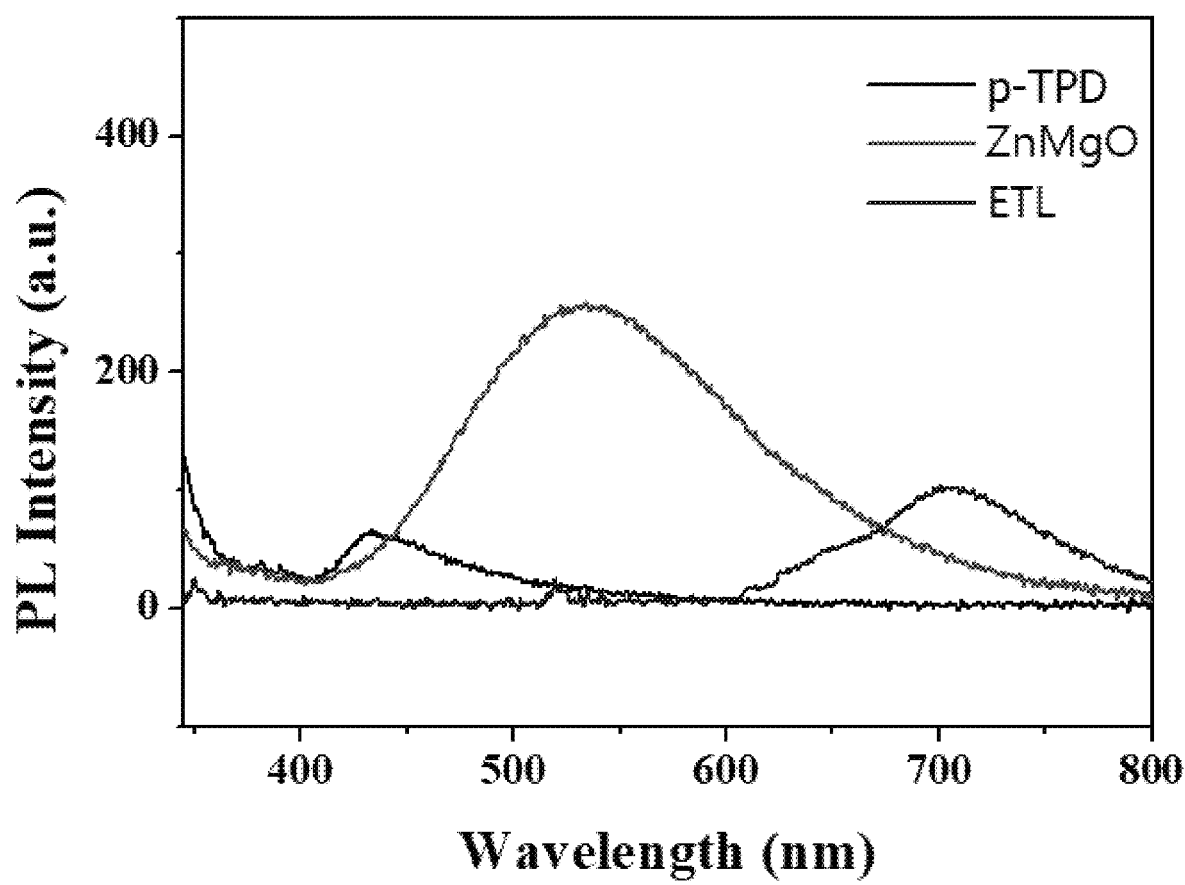
Figure 5C:
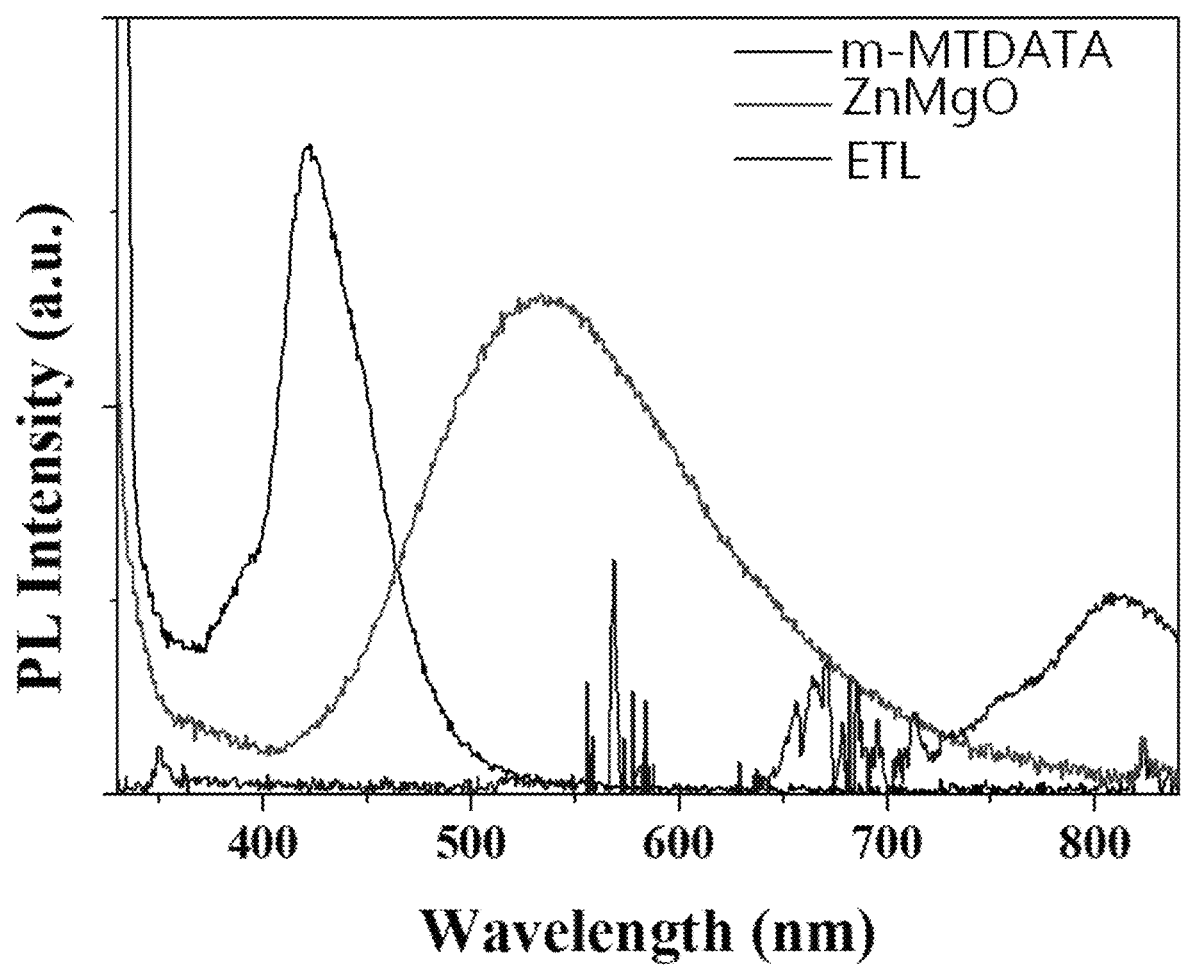

The emission wavelength of the light from the electron-property material of ZnMgO and the hole-property material of TCTA, p-TPD and m-MTDATA are measured and shown in FIGS. 5A to 5C.

When the ETL includes ZnMgO and TCTA, ZnMgO and TCTA generate the exciplex and the exciplex emission is generated. As a result, s shown in FIG. 5A, the light having a peak wavelength of about 560 nm, which is longer than a peak wavelength of each of ZnMgO and TCTA.

When the ETL includes ZnMgO and p-TPD, ZnMgO and p-TPD generate the exciplex and the exciplex emission is generated. As a result, s shown in FIG. 5B, the light having a peak wavelength of about 710 nm, which is longer than a peak wavelength of each of ZnMgO and p-TPD.

When the ETL includes ZnMgO and m-MTDATA, ZnMgO and m-MTDATA generate the exciplex and the exciplex emission is generated. As a result, as shown in FIG. 5C, the light having a peak wavelength of about 810 nm, which is longer than a peak wavelength of each of ZnMgO and m-MTDATA.

The exciplex emission wavelength range from the ETL 140 may overlap an absorption wavelength range of the QD 132 in the QD EML 130. Namely, the light having a first wavelength range is emitted from the ETL 140, and the first wavelength range overlaps at least a portion of a second wavelength range as an absorption wavelength range of the QD 132. The exciplex emission from the ETL 140 is absorbed by the QD 132, and the light is emitted again from the QD in the QD EML 130. As a result, the emission efficiency of the QD light emitting diode D is improved.

In the QD light emitting diode D of the present disclosure, it is preferred that the first electrode 110 is a transparent electrode and the second electrode 114 is a reflection electrode. Namely, the QD light emitting diode D may be a bottom-emission type.

In a top-emission type QD light emitting diode, the exciplex emission from the ETL 140 may pass through the second electrode 114 without passing through the QD EML 130 to be displayed on a display surface. In this case, the exciplex emission light from the ETL 140 and the emission light from the QD 132 are mixed such that the color purity may be degraded.

However, when the QD light emitting diode D is the bottom-emission type, since the exciplex emission light from the ETL 140 passes through the QD EML 130 and is recycled by the QD 132, the degradation of the color purity is minimized or prevented.

Figure 6:
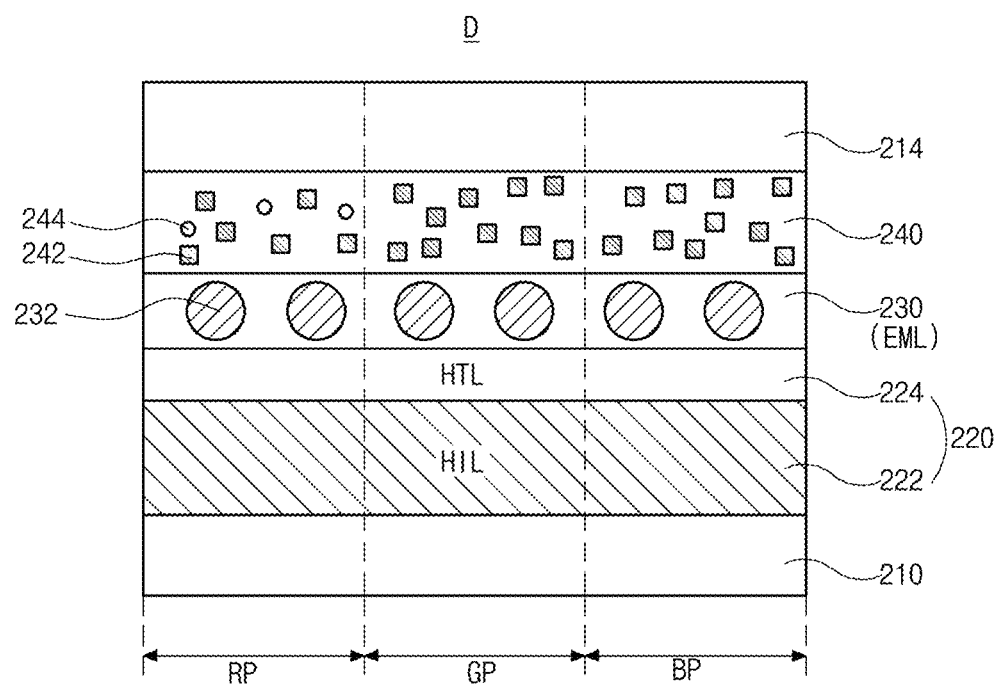
FIG. 6 is a schematic cross-sectional view of a QD light emitting diode according to a second embodiment of the present disclosure.
Figure 8A:
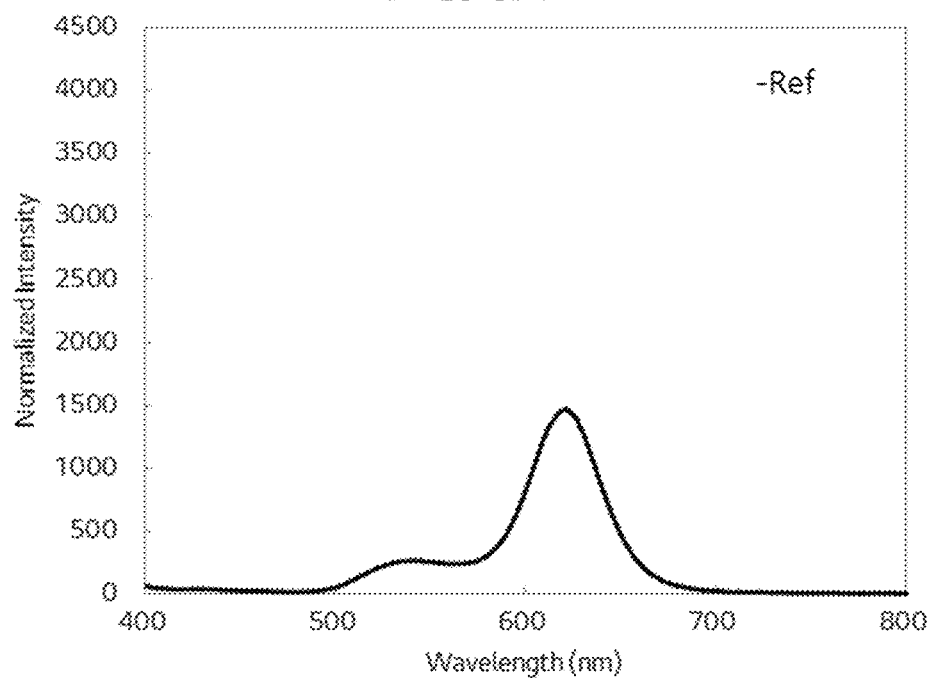
Figure 8B:
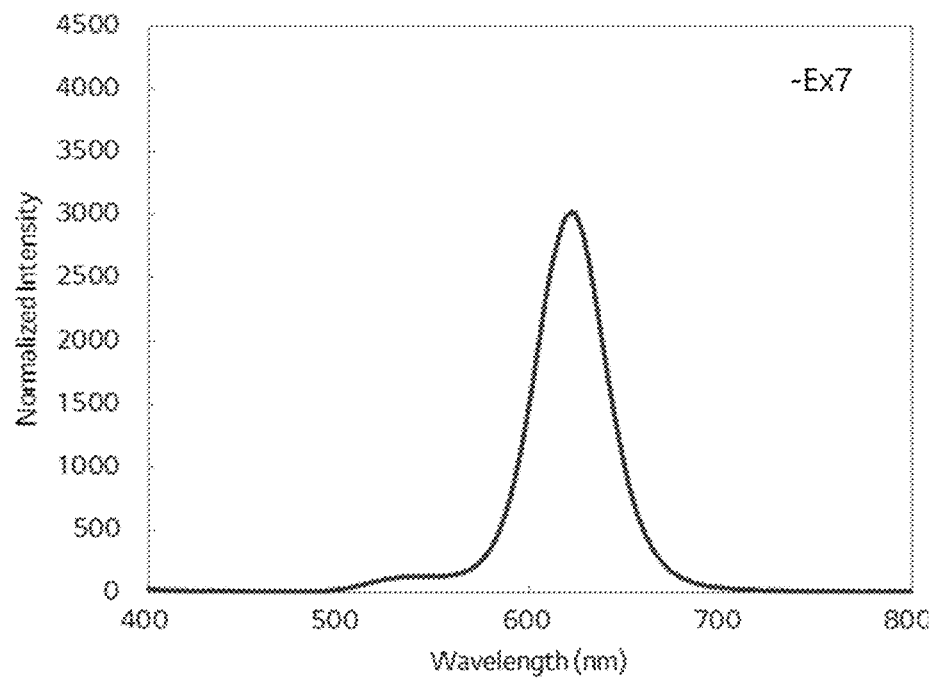
Figure 8E:
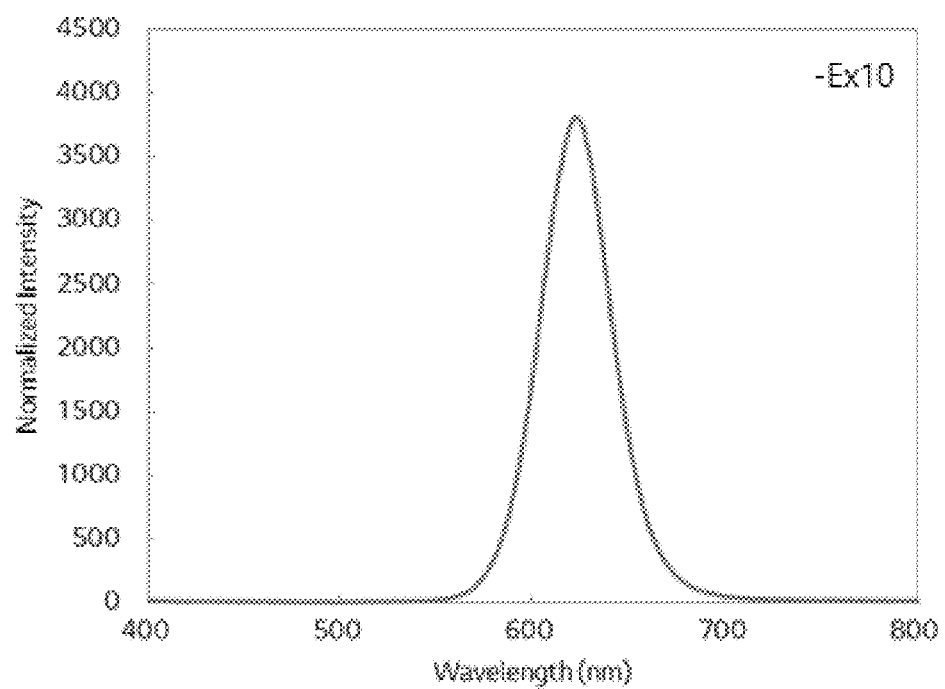
Figure 8F:
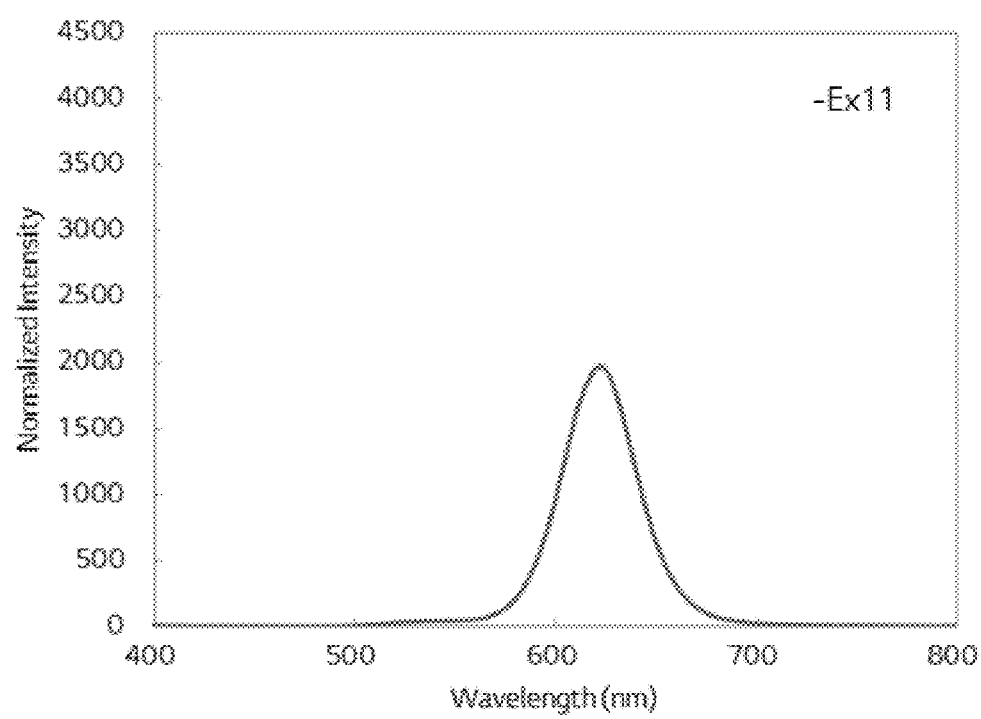
Figure 8G:
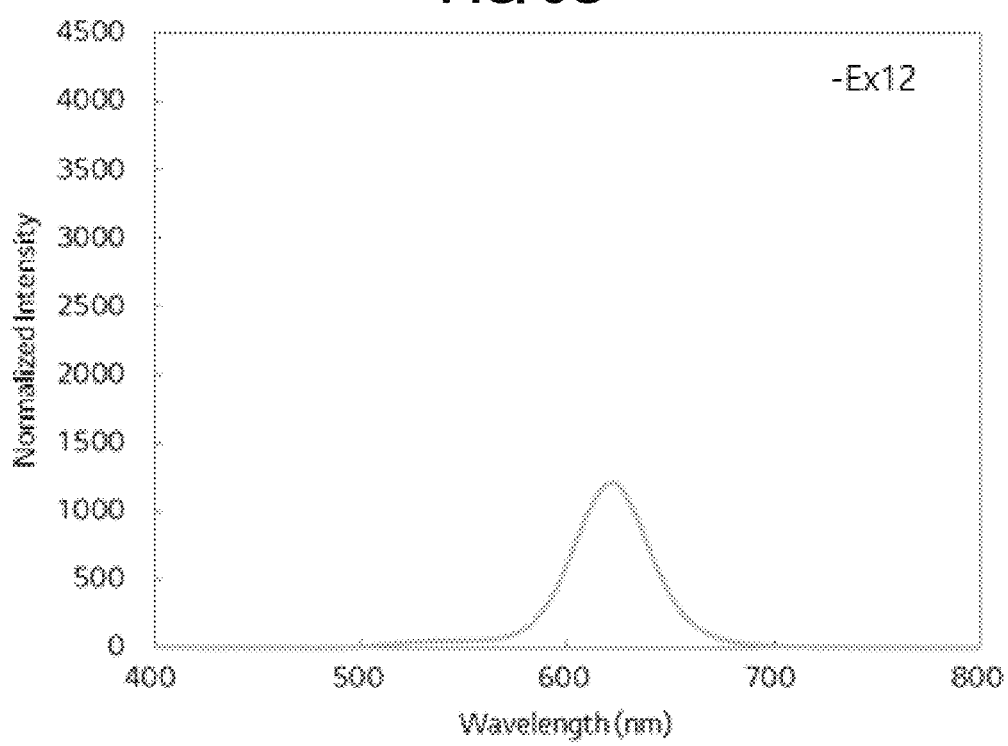

FIG. 6 is a schematic cross-sectional view of a QD light emitting diode according to a second embodiment of the present disclosure.

As shown in FIG. 6, the QD light emitting diode D according to the second embodiment of the present disclosure is disposed in each of a red pixel region Rp, a green pixel region Gp and a blue pixel region Bp and includes a first electrode 210, a second electrode 214 facing the first electrode 210 and an emitting layer 212 between the first and second electrodes 210 and 214. The emitting layer 212 includes a QD EML 230 including a QD 232, a hole auxiliary layer 220 between the first electrode 210 and the QD EML 230 and an electron auxiliary layer 240 as an electron transporting layer between the QD EML 230 and the second electrode 214.

The ETL 240 in the red pixel region Rp includes the electron-property material 242 and the hole-property material 244, and the ETL 240 in the blue pixel region Bp includes the electron-property material 242 without the hole-property material 244.

In the ETL 240 of the red pixel region Rp, the electron-property material 242 has a weight ratio greater than the hole-property material 244. For example, the weight ratio of the electron-property material 242 to the hole-property material 244 may be about 240:1 to about 6:1.

The HOMO level of the electron-property material 242 is lower than that of the hole-property material 244, and the LUMO level of the electron-property material 242 is lower than that of the hole-property material 244. For example, a HOMO level difference (ΔH) between the electron-property material 242 and the hole-property material 244 may be about 0.9 to 1.6 eV, a LUMO level difference (ΔL) between the electron-property material 242 and the hole-property material 244 may be about 1.3 to 2 eV.

A difference (ΔHL) between the HOMO level of the hole-property material 244 and the LUMO level of the electron-property material 242 may be about 1.5 to 2.5 eV, and preferably, about 1.5 to 2.2 eV. In this case, the electron-property material 242 and the hole-property material 244 form an exciplex such that the light having a peak wavelength of about 500 to 850 nm is emitted from the ETL 240.

The hole-property material 244 may be at least one of TCTA, p-TPD, m-MTDATA, TFB, PVK and VNPB of Formulas 1 to 6.

As described above, the electron-property material 242 and the hole-property material 244 generate the exciplex, and the exciplex emission light having a peak wavelength of about 500 to 850 nm is emitted from the ETL 240.

The QD 232 in the red pixel region Rp absorbs the exciplex emission light of about 500 to 850 nm from the ETL 240 and emits the light having a pre-determined wavelength range. Accordingly, the emitting efficiency and the color purity of the QD light emitting diode D in the red pixel region Rp are improved.

The QD 232 in the blue pixel region Bp has an absorption wavelength range being smaller than the exciplex emission wavelength range from the ETL 240. Accordingly, when the ETL 240 in the blue pixel region Bp include the hole-property material 244 as well as the electron-property material 242, the exciplex emission light from the ETL 240 is not absorbed by the QD 232 in the blue pixel region Bp and is provided onto a display surface.

Namely, when the ETL 240 in the blue pixel region Bp include the hole-property material 244 as well as the electron-property material 242, the charge balance is improved due to the decrease of the electron injection rate but the color purity is degraded by the exciplex emission.

Accordingly, in the QD light emitting diode D of the present disclosure, the ETL 240 in the red pixel region Rp, in which an absorption wavelength range of the QD 232 is relatively long, includes both the electron-property material 242 and the hole-property material 244 such that the improvement of the charge balance by the decrease of the electron injection rate and the improvement of the emitting efficiency by the exciplex emission are provided.

On the other hand, the ETL 240 in the blue pixel region Bp, in which an absorption wavelength range of the QD 232 is relatively short, includes the electron-property material 242 without the hole-property material 244 such that the degradation of the color purity is prevented.

In addition, since the ETL 240 can be formed by a solution process, the ETLs 240 having a difference in materials can be formed in each pixel regions without a mask process. The emitting efficiency and the color purity of the QD light emitting diode D of the present disclosure are improved without an increase of the production cost.

In FIG. 6, the ETL 240 in the green pixel region Gp includes the electron-property material 242 without the hole-property material 244. However, when the exciplex emission wavelength range by the electron-property material 242 and the hole-property material 244 overlaps the absorption wavelength range of the QD 232 in the green pixel region Gp, the ETL 240 in the green pixel region Bp may include the electron-property material 242 and the hole-property material 244.

The electron-property material 242 in the red, green and blue pixel regions are same or different, and the hole-property material 244 in the red and green pixel regions are same or different

[QD Light Emitting Diode 1]

On an anode (ITO, 50 nm), (1) an HIL (PEDOT:PSS, 40 nm), (2) an HTL (TFB, 20 nm), (3) a red QD EML (InP/ZnS, 10 nm), (4) an ETL (40 nm) and (5) a cathode (Al, 80 nm) are sequentially formed to provide a QD light emitting diode.

(1) Comparative Example (Ref)
The ETL is formed by ZnMgO.

(2) Example 1 (Ex1)
The ETL is formed by ZnMgO and TCTA (weight ratio=12:1).

(3) Example 2 (Ex2)
The ETL is formed by ZnMgO and p-TPD (weight ratio=12:1).

(4) Example 3 (Ex3)
The ETL is formed by ZnMgO and m-MTDATA (weight ratio=12:1).

(5) Example 4 (Ex4)
The ETL is formed by ZnMgO and TFB (weight ratio=12:1).

(6) Example 5 (Ex5)
The ETL is formed by ZnMgO and PVK (weight ratio=12:1).

(7) Example 6 (Ex6)
The ETL is formed by ZnMgO and VNPB (weight ratio=12:1).

The emission properties, i.e., the driving voltage, the external quantum efficiency (EQE), the luminance (Cd/m$^2$) and the lifespan, of the QD light emitting diodes in Comparative Example and Examples 1 to 6 are measured and listed in Table 2. In addition, the emission properties are shown in FIGS. 7A to 7D.

TABLE 2

|  | V (10 J) | EQE (10 J) | Cd/m$^2$ (10 J) | Lifespan (@T$_{50}$) |
| --- | --- | --- | --- | --- |
| Ref | 4.4 | 4.55 | 460.3 | 0.43 h |
| Ex1 | 4.01 | 6.67 | 663.9 | 3.09 h |
| Ex2 | 3.7 | 4.89 | 497.5 | 2.34 h |
| Ex3 | 4.36 | 4.97 | 498.1 | 1.34 h |
| Ex4 | 3.7 | 5.27 | 536.4 | 2.25 h |
| Ex5 | 3.6 | 5.26 | 531.1 | 2.08 h |
| Ex6 | 3.57 | 5.86 | 589.3 | 2.83 h |

As shown in Table 2 and FIGS. 7A to 7D, the ETL in the QD light emitting diode (Ex1 to Ex6) of the present disclosure includes the electron-property material and the hole-property material such that the emitting efficiency and the lifespan of the QD light emitting diode are significantly increased.

[QD Light Emitting Diode 2]

The QD light emitting diode having the same structure as the QD light emitting diode in Examples 1 to 6 except a material of the ETL is provided. The materials in Table 3 are used as the material of the ETL. The emission spectrum of the QD light emitting diode in Comparative Example and Examples 7 to 12 is shown in FIGS. 8A to 8G.

TABLE 3

|  | ZnMgO (24 mg/ml) | TCTA (1 mg/ml) |
| --- | --- | --- |
| Ex7 | 1 | 0.1 |
| Ex8 | 1 | 0.5 |
| Ex9 | 1 | 1 |
| Ex10 | 0.5 | 1 |
| Ex11 | 0.25 | 1 |
| Ex12 | 0.125 | 1 |

As shown in FIGS. 8A to 8G, in comparison to the emission intensity of the QD light emitting diode in Comparative Example (FIG. 8A), the emission intensity of the QD light emitting diode including the ETL, which includes the electron-property material and the hole-property material, is increased.

On the other hand, the amount (weight ratio) of the hole-property material in the ETL is over a pre-determined range, the emitting efficiency of the QD light emitting diode is decreased. Accordingly, the weight ratio of the electron-property material to the hole-property material in the ETL may be about 240:1 to about 12:1.

As described above, in the QD light emitting diode of the present disclosure, since the ETL includes the electron-property material and the hole-property material, the charge balance in the QD light emitting diode and the QD light emitting display device is improved such that the emitting efficiency and the lifespan are increased. In addition, since the electron-property material and the hole-property material in the ETL provides the exciplex emission, the emitting efficiency of the QD light emitting diode and the QD light emitting display device is further increased.

It will be apparent to those skilled in the art that various modifications and variations can be made in the aspects of the disclosure without departing from the spirit or scope of the disclosure. Thus, it is intended that the present disclosure covers the modifications and variations of this disclosure provided they come within the scope of the appended claims and their equivalents.

What is claimed is:

1. A quantum dot (QD) light emitting diode, comprising:
   a first electrode and a second electrode facing each other;
   a QD emitting material layer positioned between the first electrode and the second electrode and including a QD;
   a hole auxiliary layer positioned between the first electrode and the QD emitting material layer; and
   an electron transporting layer positioned between the QD emitting material layer and the second electrode and including an electron-property material and a hole-property material,
   wherein:
   the electron-property material is a zinc oxide material,
   the hole-property material is at least one of the following materials:

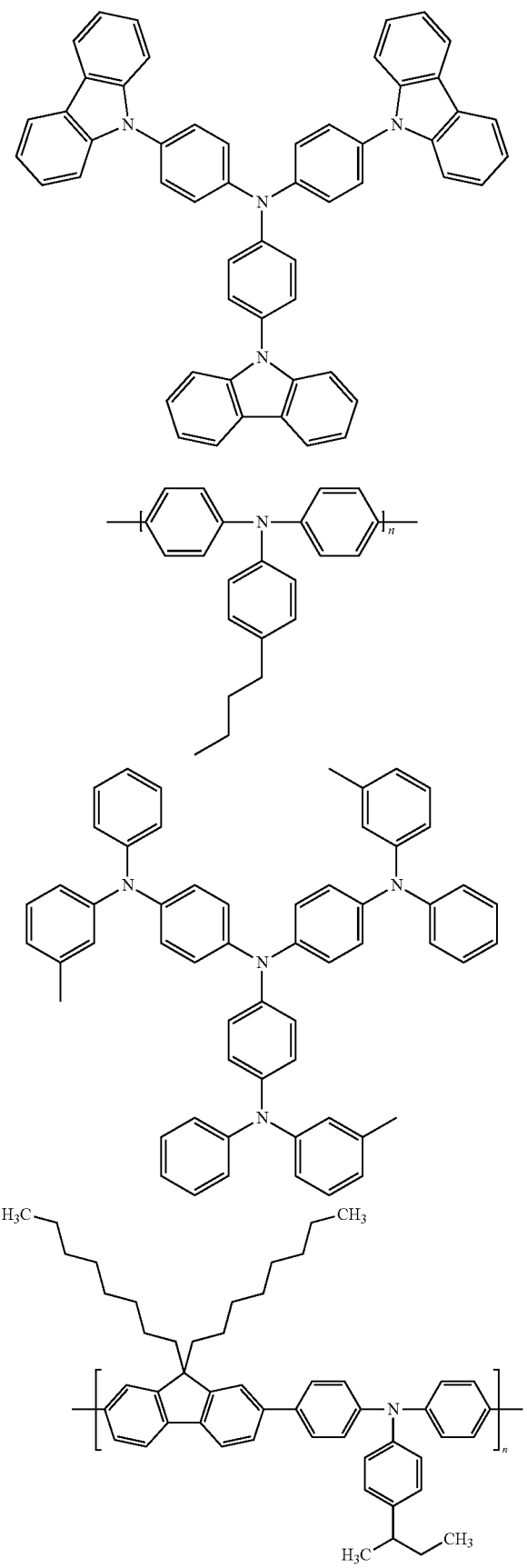

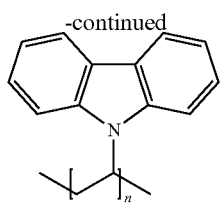
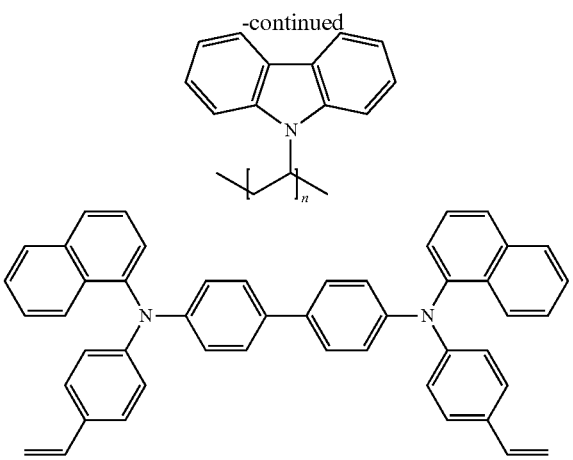

and n is an integer of 1 to 10000.

2. The QD light emitting diode according to claim 1, wherein a HOMO level difference between the electron-property material and the hole-property material is about 0.9 to 1.6 eV, and a LUMO level difference between the electron-property material and the hole-property material is about 1.3 to 2 eV.

3. The QD light emitting diode according to claim 1, wherein a difference between a HOMO level of the hole-property material and a LUMO level of the electron-property material is about 1.5 to 2.5 eV.

4. The QD light emitting diode according to claim 1, wherein the electron-property material has a weight ratio greater than the hole-property material.

5. The QD light emitting diode according to claim 4, wherein the weight ratio of the electron-property material to the hole-property material is about 240:1 to about 6:1.

6. The QD light emitting diode according to claim 1, wherein a light having a first wavelength range is emitted from the electron transporting layer, and the first wavelength range overlaps at least a portion of a second wavelength range as an absorption wavelength range of the QD.

7. A QD light emitting display device, comprising:
a substrate including a red pixel region, a green pixel region and a blue pixel region;
a QD light emitting diode positioned on or over the substrate, the QD light emitting diode including:
a first electrode and a second electrode facing each other;
a QD emitting material layer positioned between the first electrode and the second electrode and including a QD;
a hole auxiliary layer positioned between the first electrode and the QD emitting material layer; and
an electron transporting layer positioned between the QD emitting material layer and the second electrode; and
a thin film transistor positioned between the substrate and the QD light emitting diode and connected to the QD light emitting diode,
wherein:
the electron transporting layer in the red pixel region includes an electron-property material and a hole-property material, and
the electron transporting layer in the blue pixel region includes the electron-property material and excludes the hole-property material.

8. The QD light emitting display device according to claim 7, wherein the electron-property material in the blue pixel region is same as or different from the electron-property material in the red pixel region.

9. The QD light emitting display device according to claim 7, wherein the electron transporting layer in the green pixel region includes the electron-property material and excludes the hole-property material.

10. The QD light emitting display device according to claim 9, wherein the electron-property material in the green pixel region is same as or different from the electron-property material in the red pixel region.

11. The QD light emitting display device according to claim 7, wherein the electron transporting layer in the green pixel region includes the electron-property material and the hole-property material.

12. The QD light emitting display device according to claim 11, wherein the hole-property material in the green pixel region is same as or different from the hole-property material in the red pixel region.

13. The QD light emitting display device according to claim 7, wherein a HOMO level difference between the electron-property material and the hole-property material is about 0.9 to 1.6 eV, and a LUMO level difference between the electron-property material and the hole-property material is about 1.3 to 2 eV.

14. The QD light emitting display device according to claim 7, wherein a difference between a HOMO level of the hole-property material and a LUMO level of the electron-property material is about 1.5 to 2.5 eV.

15. The QD light emitting display device according to claim 7, wherein in the electron transporting layer in the red pixel region, the electron-property material has a weight ratio greater than the hole-property material.

16. The QD light emitting display device according to claim 15, wherein the weight ratio of the electron-property material to the hole-property material is about 240:1 to about 6:1.

17. The QD light emitting display device according to claim 7, wherein:
the electron-property material is a zinc oxide material,
the hole-property material is at least one of the following materials:

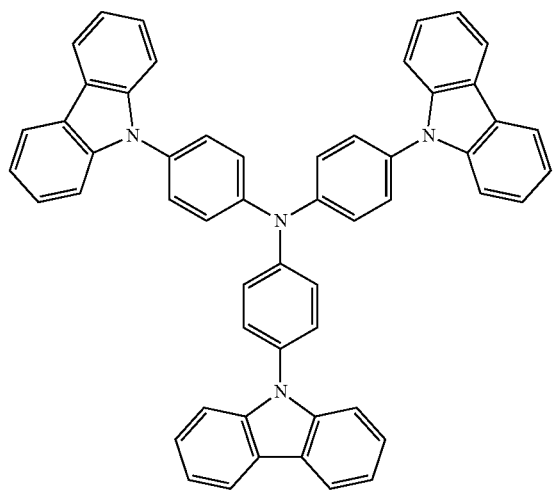

-continued

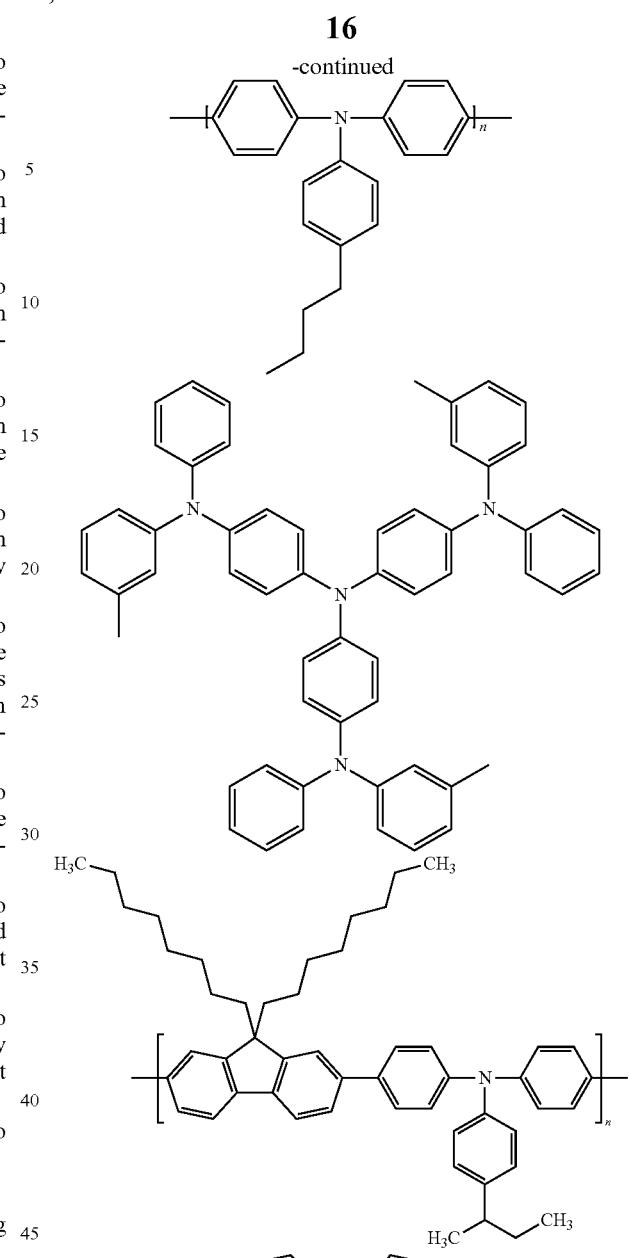

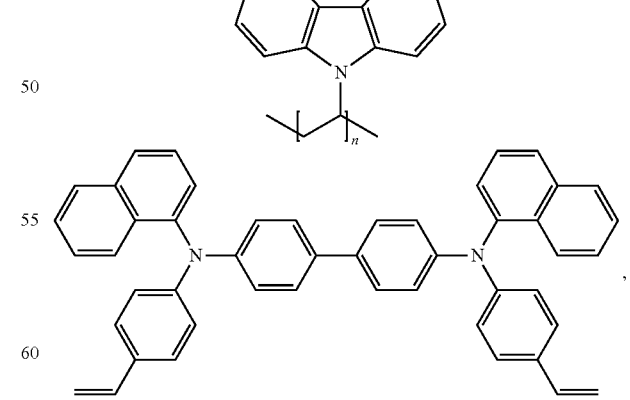

and n is an integer of 1 to 10000.

18. The QD light emitting display device according to claim 7, wherein a light having a first wavelength range is emitted from the electron transporting layer in the red pixel region, and the first wavelength range overlaps at least a portion of a second wavelength range as an absorption wavelength range of the QD in the red pixel region.

19. A quantum dot (QD) light emitting diode, comprising:
a first electrode and a second electrode facing each other;
a QD emitting material layer positioned between the first electrode and the second electrode and including a QD;
a hole auxiliary layer positioned between the first electrode and the QD emitting material layer; and
an electron transporting layer positioned between the QD emitting material layer and the second electrode and including an electron-property material and a hole-property material,
wherein an electron mobility of the electron-property material is greater than a hole mobility of the electron-property material, and a hole mobility of the hole-property material is greater than an electron mobility of the hole-property material.

20. The QD light emitting diode according to claim 19, wherein the electron-property material and the hole-property material are mixed in the electron transporting layer.

* * * * *